United States Patent
Atwah

(10) Patent No.: US 11,860,137 B2
(45) Date of Patent: Jan. 2, 2024

(54) METHOD FOR DETECTING NATURAL HYDROCARBONS IN OIL-CONTAMINATED DRILL CUTTINGS

(71) Applicant: SAUDI ARABIAN OIL COMPANY, Dhahran (SA)

(72) Inventor: Ibrahim Atwah, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 14 days.

(21) Appl. No.: 17/648,458

(22) Filed: Jan. 20, 2022

(65) Prior Publication Data

US 2023/0228721 A1    Jul. 20, 2023

(51) Int. Cl.
G01N 30/72    (2006.01)

(52) U.S. Cl.
CPC .............................. *G01N 30/7206* (2013.01)

(58) Field of Classification Search
CPC ................................................. G01N 30/7206
See application file for complete search history.

(56) References Cited

U.S. PATENT DOCUMENTS

| | | | |
|---|---|---|---|
| 6,514,915 B1 | 2/2003 | Beyer et al. | |
| 8,932,872 B2 * | 1/2015 | Reppas | C12P 5/02 436/139 |
| 9,388,332 B2 | 7/2016 | Deville et al. | |
| 10,921,307 B2 | 2/2021 | Inan | |
| 2006/0144588 A1 | 7/2006 | Ferguson et al. | |

(Continued)

FOREIGN PATENT DOCUMENTS

CA    2741791 C    2/2016

OTHER PUBLICATIONS

Carvajal-Ortiz, H. and T. Gentzis, "Critical considerations when assessing hydrocarbon plays using Rock-Eval pyrolysis and organic petrology data: Data quality revisited", International Journal of Coal Geology, ScienceDirect, Elsevier B.V., vol. 152, Jun. 2015, pp. 113-122 (10 pages).

(Continued)

*Primary Examiner* — Peter J Macchiarolo
*Assistant Examiner* — John M Royston
(74) *Attorney, Agent, or Firm* — Osha Bergman Watanabe & Burton LLP

(57) ABSTRACT

Described is a method for detecting the presence of natural hydrocarbon compounds in drilling cuttings. The method includes introducing a chemical standard to an oil-based drilling fluid, producing a tagged drilling fluid. Gas chromatography-mass spectroscopy (GC-MS) is used to determine a concentration of hydrocarbon compounds in the tagged drilling fluid, which corresponds to a first hydrocarbon signal. The tagged drilling fluid is circulated in a borehole during drilling, and the drilling cuttings mixed with the tagged drilling fluid are recovered. Hydrocarbon compounds are then extracted from the drilling cuttings. GC-MS is used to determine a concentration of hydrocarbon compounds present in the drilling cuttings that were mixed with the tagged drilling fluid, which corresponds to a second hydrocarbon signal. Based on the difference between the first and second hydrocarbon signals, an initial concentration of natural hydrocarbons in the drilling cuttings prior to mixing with the tagged drilling fluid is determined.

10 Claims, 5 Drawing Sheets

(56) References Cited

U.S. PATENT DOCUMENTS

| | | |
|---|---|---|
| 2008/0105032 A1 | 5/2008 | Reddy et al. |
| 2014/0208825 A1 | 7/2014 | Holba et al. |
| 2014/0208826 A1 | 7/2014 | Larter et al. |
| 2018/0284096 A1 | 10/2018 | Brierley |
| 2019/0226326 A1 | 7/2019 | Ow et al. |
| 2019/0360326 A1* | 11/2019 | Deville ............... E21B 49/005 |
| 2020/0116019 A1 | 4/2020 | Ow et al. |
| 2021/0246365 A1 | 8/2021 | Borrell et al. |

OTHER PUBLICATIONS

Inan, Sedat, et al., "Thermo-vaporization for decontaminating hydrocarbon source rocks", International Journal of Coal Geology, ScienceDirect, Elsevier B.V., vol. 189, Mar. 2018, pp. 111-121 (11 pages).

Ohm, S.E., et al., "A drilling mud additive influencing the geochemical interpretations of hydrocarbon shows", Petroleum Geoscience, EAGE/Geological Society of London, vol. 13, 2007, pp. 369-376 (8 pages).

* cited by examiner

METHOD FOR DETECTING NATURAL HYDROCARBONS IN OIL-CONTAMINATED DRILL CUTTINGS

BACKGROUND

Drilling cuttings, also referred to as rock chips, are small rock fragments collected during drilling a wellbore. The drilling cuttings contain crucial geological information regarding hydrocarbon-bearing zones. During drilling, geologists can utilize drilling cuttings to extract crucial information in order to identify different geological layers and their potential for containing hydrocarbons. However, drilling cuttings that are recovered from wells drilled with oil-based fluids material are often artificially contaminated with hydrocarbons. Rock contamination by drilling fluid is problematic because it hinders the detection of natural hydrocarbon in recovered drilling cuttings. Such contamination overprints the signal of natural hydrocarbon, making the assessment of the reservoir interval difficult.

Accordingly, there exists a need for removing a contamination signal from contaminated rock chips to detect an initial amount of natural hydrocarbons prior to contamination.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for detecting the presence of natural hydrocarbon compounds in drilling cuttings. The method includes introducing a synthetic chemical standard having a known concentration to an oil-based drilling fluid, which produces a tagged oil-based drilling fluid. Using gas chromatography-mass spectroscopy, a concentration of hydrocarbon compounds present in the tagged oil-based drilling fluid is determined. This concentration corresponds to a first hydrocarbon signal. The tagged oil-based drilling fluid is then circulated in a borehole during drilling. Recovered drilling cuttings are mixed with the tagged oil-based drilling fluid from the borehole, and hydrocarbon compounds are extracted from the drilling cuttings. Using gas chromatography-mass spectroscopy, a concentration of hydrocarbon compounds present in the drilling cuttings that were mixed with the tagged oil-based drilling fluid is determined. This concentration corresponds to a second hydrocarbon signal. Based on the difference between the first hydrocarbon signal and the second hydrocarbon signal, an initial concentration of natural hydrocarbons in the drilling cuttings prior to mixing with the tagged oil-based drilling fluid is determined.

In another aspect, embodiments disclosed herein relate to a system for detecting the presence of natural hydrocarbon compounds in drilling cuttings. The system includes a drilling bit configured for cutting into rock in a borehole, a drilling cuttings collector configured for recovering drilling cuttings that were mixed with an oil-based drilling fluid tagged with a synthetic chemical standard having a known concentration during drilling, a hydrocarbon detection unit configured for extracting hydrocarbon compounds from the drilling cuttings, and a gas-chromatograph equipped with a mass-spectrometer. The mass-spectrometer is configured for determining a concentration of hydrocarbon compounds present in the tagged oil-based drilling fluid, where the concentration corresponds to a first hydrocarbon signal; and determining a concentration of hydrocarbon compounds present in the drilling cuttings that were mixed with the tagged oil-based drilling fluid, where the concentration corresponds to a second hydrocarbon signal. The system further includes a computing system configured for determining, based on the difference between the first hydrocarbon signal and the second hydrocarbon signal, an initial concentration of natural hydrocarbons in the drilling cuttings prior to mixing with the tagged oil-based drilling fluid.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1A:
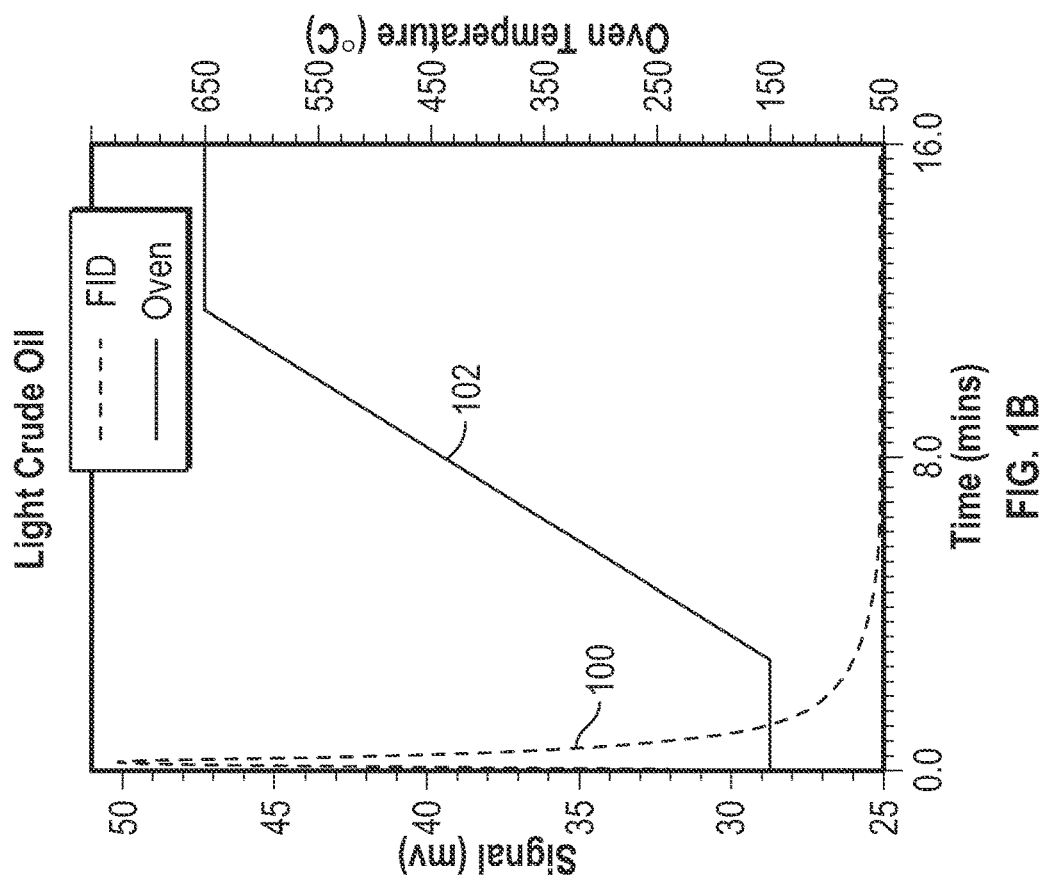
FIG. 1A is a plot illustrating the composition of drilling fluids using a pyrolysis flame ionization detector according to embodiments of the present disclosure.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method and a system for detecting the presence of hydrocarbons in drilling cuttings through the addition of an artificial chemical standard to the drilling fluids. More specifically, the artificial chemical standard is used to accurately measure the amount of drilling fluid contaminates on the recovered drilling cuttings, also referred to as rock chips, from the borehole. The contamination signal from the drilling fluid hydrocarbons is then subtracted from the contamination signal of the contaminated rock chips to reveal an initial amount of natural hydrocarbons in the sample prior to contamination. Each of these aspects will be described in further detail below.

During drilling, geologists utilize drilling cuttings to extract crucial information in order to identify different geological layers and their potential for containing hydrocarbons. However, drilling cuttings that are recovered from wells drilled with oil-based fluids material are often artificially contaminated with hydrocarbons. Such oil-based fluids, when mixed with drilling cuttings in the borehole, will result in overprinting the natural hydrocarbon signal in drilling cuttings. This is typically identified using pyrolysis and gas chromatography-mass spectrometry (GC-MS) techniques.

Figure 1B:
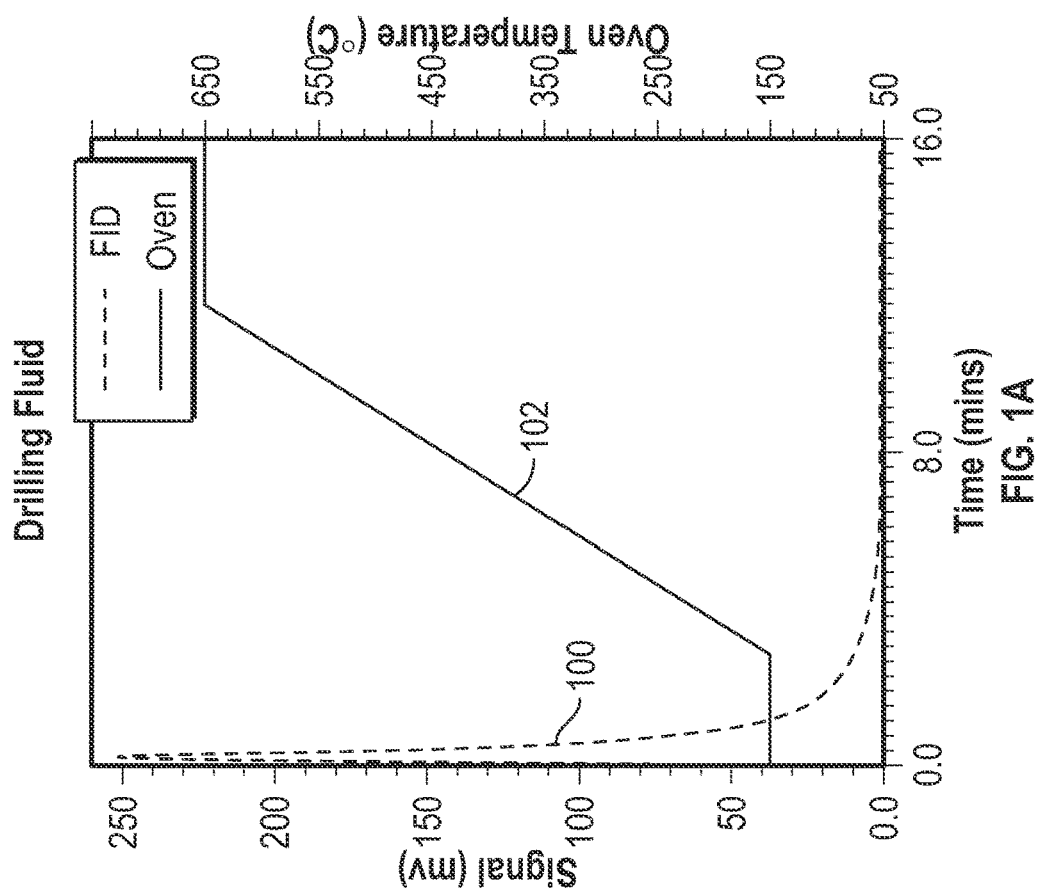
FIG. 1B is a plot illustrating the composition of light crude oil using a pyrolysis flame ionization detector according to embodiments of the present disclosure.

Turning now to FIGS. 1A-1D, FIGS. 1A-1D depict a close similarity in composition between oil-based drilling fluids and natural hydrocarbons in crude oil and rock extracts. Specifically, FIGS. 1A and 1B illustrate a comparison between the composition of drilling fluids (FIG. 1A) and light crude oil (FIG. 1B) using a pyrolysis flame ionization detector. In FIGS. 1A and 1B, curve (100) represents flame ionization detector (FID) values over time, and curve (102) represent values obtained from an oven that controls the temperature over time.

Figure 1D:
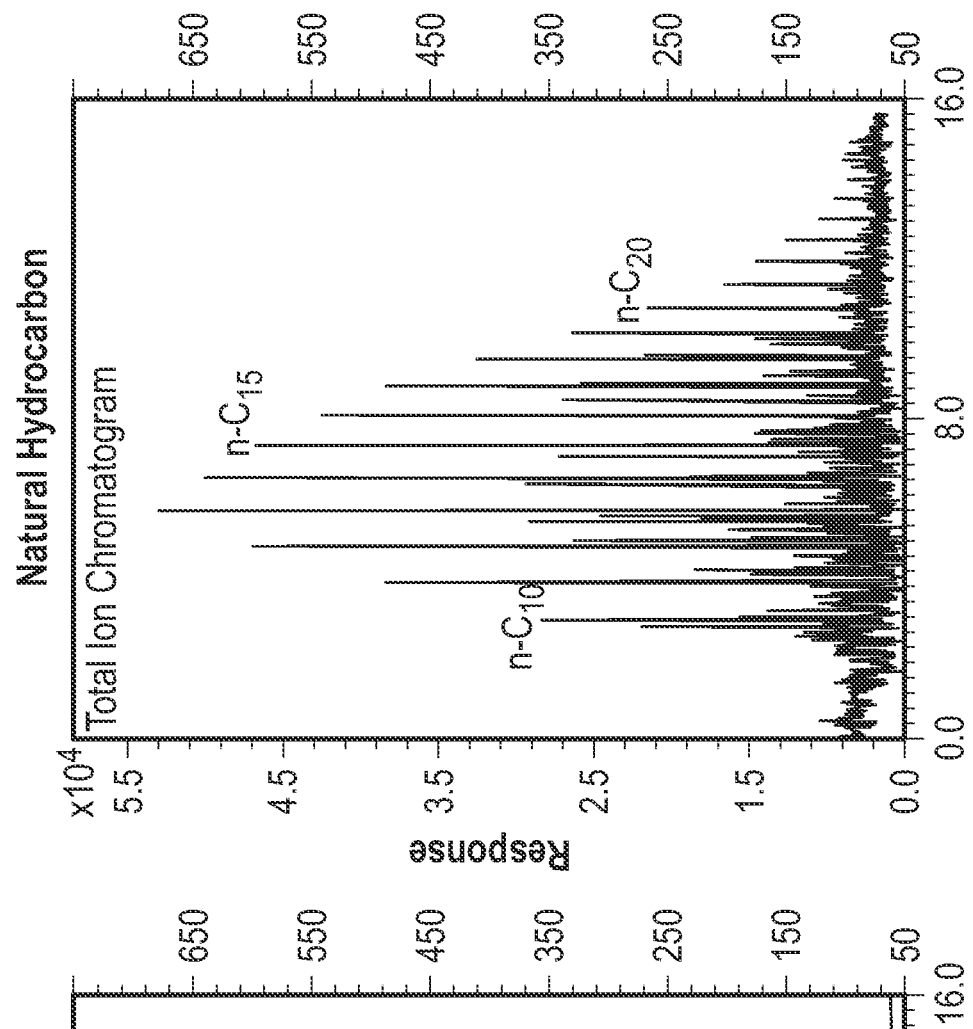
FIG. 1D is a plot illustrating the composition of natural hydrocarbons from rock extracts using total ion chromatogram obtained from GC-MS analysis according to embodiments of the present disclosure.
Figure 1C:
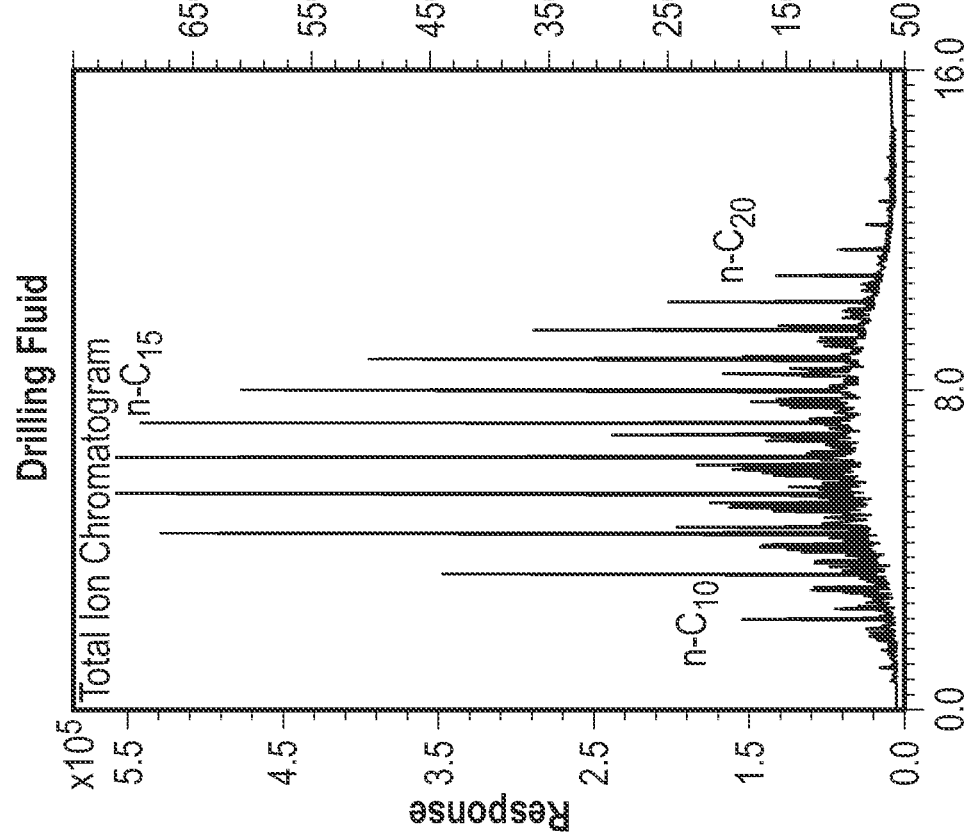
FIG. 1C is a plot illustrating the composition of drilling fluids using total ion chromatogram obtained from gas chromatography-mass spectrometry (GC-MS) analysis according to embodiments of the present disclosure.

Referring to FIGS. 1C and 1D, a comparison between the composition of drilling fluids (FIG. 1C) and natural hydrocarbons from rock extracts (FIG. 1D) using total ion chromatogram obtained from GC-MS analysis is depicted. The labeled peaks depict the abundance of straight-chain hydrocarbons ranging in carbon number from $C_{10}$ to $C_{24}$.

Oil-based drilling fluids contain a series of n-alkane hydrocarbons at the diesel range, with carbon number and a molecular weight ranging from normal decane (n-$C_{10}$) to tetracosane (n-$C_{24}$). Carbon number is the total number of carbon atoms contained in a hydrocarbon or other chemical's molecule. A hydrocarbon is any of a class of organic chemicals made up of only the elements carbon (C) and hydrogen (H). Hydrocarbon type refers to the type of chemical bonds between the carbon atoms and other parts of the molecule. Hydrocarbon type includes monoaromatic (substituted benzene), naphthalene, fluorene, anthracene, olefin, iso-olefin (alkene or alkyne), olefino-naphthene, mono-naphthene (cycloalkane), decalin, indane, indene, tetralin, paraffin, isoparaffin (alkane), nitrogen, sulfur and oxygen (NSO) compounds, asphaltenes, alcohol, ether, ester, ketone, and aldehyde. Alkanes contain only single bonds, alkenes contain a carbon-carbon double bond, alkynes contain a carbon-carbon triple bond, and aromatics contain a benzene ring. The composition of oil-based drilling fluids appears in the pyrolysis instrument as one peak (refer to FIG. 1A), which is also similar to the same signal of light crude oil (refer to FIG. 1B). Therefore, pyrolysis analysis is considered unreliable for rock samples contaminated with drilling fluid. In addition, the GC-MS signal of an oil-based mud (FIG. 1C) is closely similar to the natural hydrocarbon signal obtained from rock extracts (FIG. 1D), which can negatively impact a number of geochemical parameters.

Described herein is a method for detecting the presence of natural hydrocarbons in drilling cuttings through the addition of a synthetic chemical standard, having a known concentration, to the drilling fluids. The addition of the synthetic chemical standard must be introduced prior to circulating the drilling fluid through the borehole, such that, the drilling mud at the mud pit contains the drilling fluids with the added synthetic chemical compound.

Figure 2:
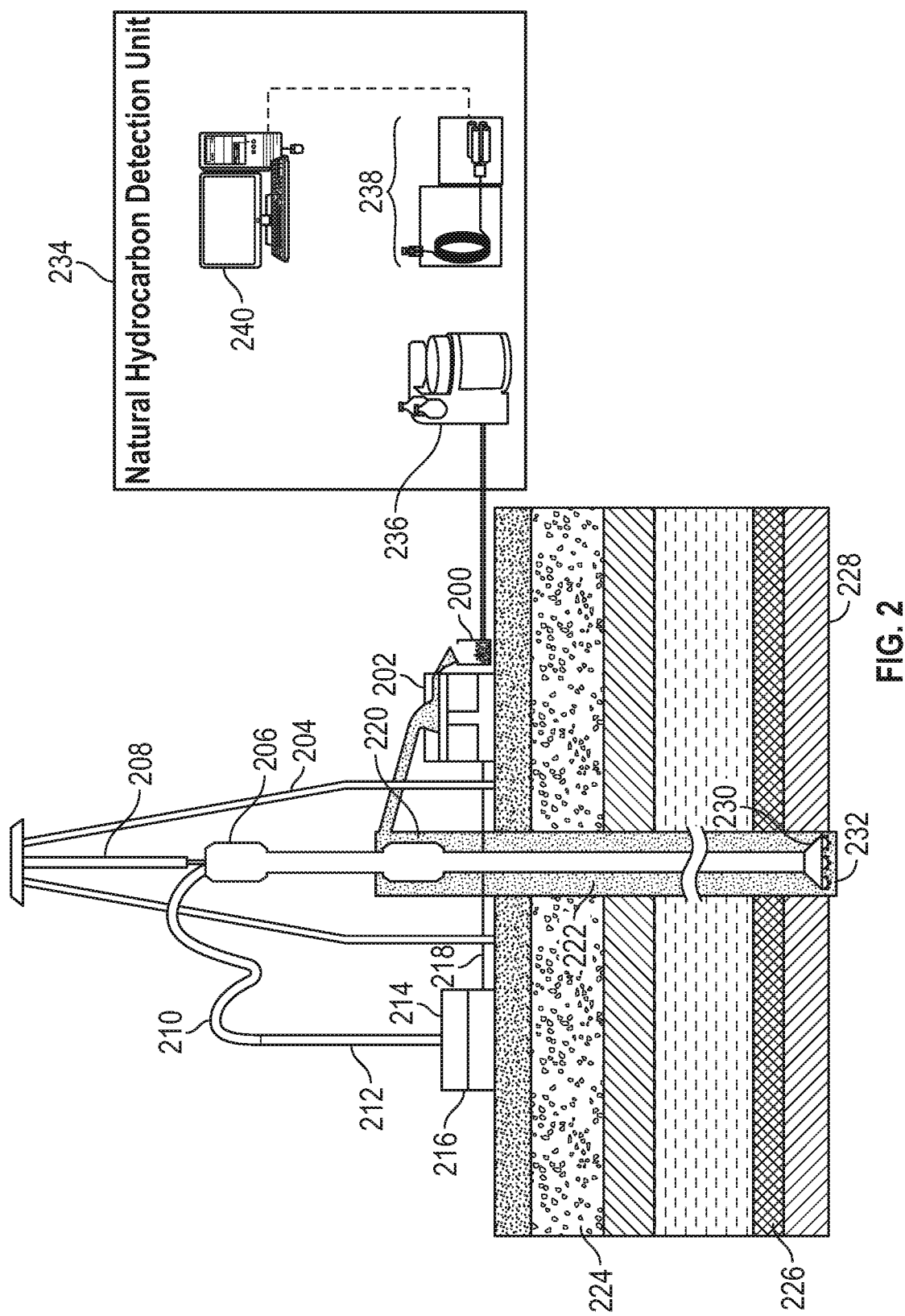
FIG. 2 is a cross-sectional view illustration of a drilling well site according to embodiments of the present disclosure.

FIG. 2 illustrates an exemplary drilling well site. In general, well sites may be configured in a myriad of ways. Therefore, the drilling well site depicted in FIG. 2 is not intended to be limiting with respect to the particular configuration of the drilling equipment. The drilling well site is depicted as being on land. In other examples, the well site may be offshore, and drilling may be carried out with or without use of a marine riser. A drilling operation at the well site may include drilling a wellbore into a subsurface including various formations. In one or more embodiments, the well site may include a drilling cuttings collector (200) and a mud tank with a shale shaker (202) at the top. A drill string may be suspended in the wellbore by a derrick (204) with a swivel (206) and a kelly (208) extending down from the top of the derrick (204) and attached to a rotary house (210), which rotates the drill string, and a standpipe (212).

Furthermore, in one or more embodiments, the drilling site may comprise a drilling mud pump (214). Mixed mud (216) is collected proximate the rig site surface (218) at which the drill pipe (220) extends down the borehole (222). The borehole (222) can penetrate a number of geological formations, including an overburden layer (224), a tight-sealing shale layer (226), and a hydrocarbon-bearing reservoir layer (228). The drilling site may further include a drilling bit (230) to cut into the subsurface rock. While penetrating the reservoir layer (228), the drilling bit (230) reaches a deepest reservoir zone (232) of the wellbore at which drill cuttings are recovered and circulated to the surface.

In one or more embodiments, recovered drilling cuttings are transferred to a natural hydrocarbon detection unit (234). The hydrocarbon detection unit (234) may include an organic solvent extractor (236), which produces the rock extracts. Solvent extraction is the separation and/or concentration of components of a solution by distribution between two immiscible liquid phases. Solvent extraction provides the ability to separate mixtures into components according to their chemical type. The rock extracts may then be analyzed on a gas-chromatograph equipped with a mass-spectrometer (238) (GC-MS), and processing can be performed at a data output, display, and processing module (240). The processing module (240) may be implemented in hardware (i.e., circuitry), software, or any combination thereof. In one embodiment, the GC-MS is a triple quadrupole mass spectrometer, or GC-MS-QQQ. The GC-MS-QQQ is a tandem mass spectrometer consisting of two quadrupole mass analyzers in series with a radio frequency (RF)-only quadrupole between them to act as a cell for collision-induced dissociation. The GC-MS-QQQ allows for increased sensitivity and specificity, resulting in lower detection and quantitation limits.

Figure 3:
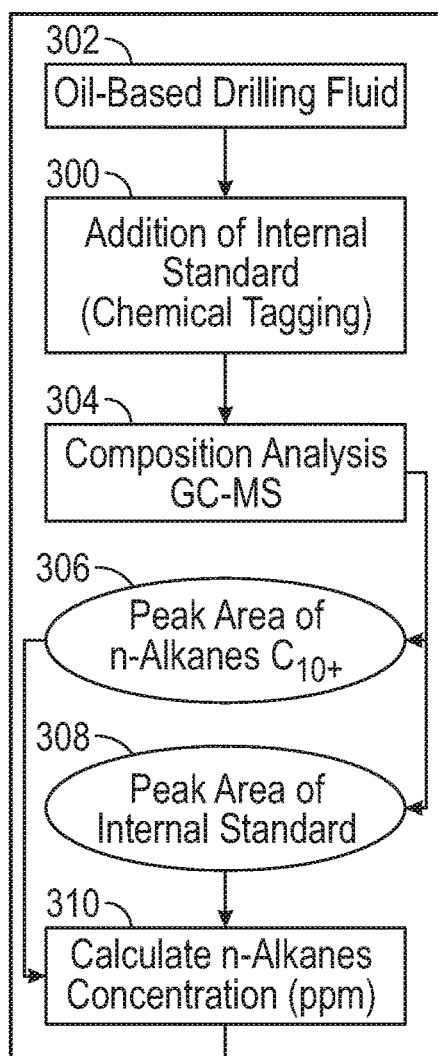
FIG. 3 is a flowchart illustrating a method for tagging and calibration of oil-based drilling fluids with a synthetic chemical standard and detecting natural hydrocarbons in rock cuttings contaminated with tagged oil-based drilling fluid according to embodiments of the present disclosure.
Figure 3:
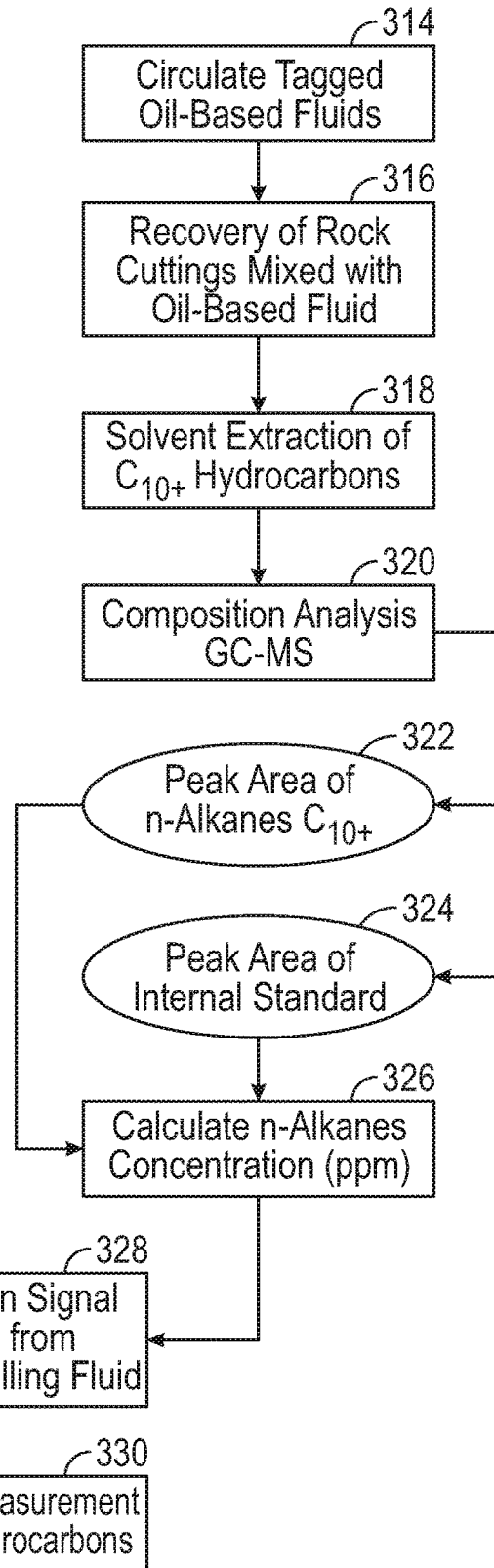

Referring to FIG. 3, FIG. 3 is a flowchart depicting the workflows for establishing the detection of natural hydrocarbon in drilling cuttings contaminated with oil-based drilling fluids. The flowchart illustrates steps for tagging and calibration of oil-based drilling fluids with a synthetic chemical standard according to embodiments of this disclosure. Additionally, the flowchart illustrates the process for detecting natural hydrocarbons in rock cuttings contaminated with tagged oil-based drilling fluid described herein.

In one or more embodiments, the method is divided into two main stages. The first stage is directed to tagging and calibration of the oil-based drilling fluids, while the second stage is directed to detection of natural hydrocarbon in the contaminated drill cuttings. A first step (300) of the first stage is addition of an internal synthetic chemical standard to the oil-based drilling fluid (302) at a known concentration. This addition of a synthetic chemical standard is referred to as chemical tagging. A non-limiting example of a synthetic chemical standard is 1-pentadecene, but any suitable chemical standard having the same chemical properties can be utilized. The synthetic chemical standard allows for accurate concentration quantification of all hydrocarbon compounds present in the oil-based drilling fluids, as will be described in detail below.

In a second step 304, the mixture of the drilling fluid and internal synthetic chemical standard is analyzed using a gas chromatography-mass spectrometry (GC-MS) analytical approach, resulting in a peak area of n-alkanes $C_{10+}$ (306) and a peak area of internal standard (308). In a third step (310), the concentration of each individual hydrocarbon compound in parts per million (PPM) is determined as follows:

$$\text{HC concentration} = \frac{HCa}{STa} \times STc \times F, \quad (1)$$

where HCa denotes the hydrocarbon peak area (306) from the instrument signal, STa denotes the peak area of added internal chemical standard (308), STc denotes the concentration of the internal chemical standard, and F denotes the instrument response factor. The instrument response factor is a ratio of an analyte of interest signal response and the standard internal concentration. In some embodiments, the value for the instrument response factor can range from 0.3 to 4 based on many factors related to the instrument operation condition. After determining the concentration of each hydrocarbon compound in the drilling fluids, a calibration relationship for all n-alkanes is established in a fourth step (312). The calibration relationship is a ratio factor for each compound relative to the internal synthetic chemical standard, as shown in the table of mass chromatography data below.

TABLE 1

| Input (Drilling fluids with internal standard) | | | Analysis (Recovered drilling cuttings from borehole) | Output (Measured natural hydrocarbons) |
| --- | --- | --- | --- | --- |
| Compound Label * | Concentration (ppm) | Ratio Factor | Concentration (ppm) | Concentration (ppm) |
| n-$C_{10}$ | 5669.57 | 0.22 | 5799.60 | 130.03 |
| n-$C_{11}$ | 16247.83 | 0.64 | 16438.78 | 190.95 |
| n-$C_{12}$ | 26865.22 | 1.05 | 27112.26 | 247.04 |
| n-$C_{13}$ | 29421.74 | 1.15 | 29703.04 | 281.30 |

TABLE 1-continued

| Input (Drilling fluids with internal standard) | | | Analysis (Recovered drilling cuttings from borehole) | Output (Measured natural hydrocarbons) |
| --- | --- | --- | --- | --- |
| Compound Label * | Concentration (ppm) | Ratio Factor | Concentration (ppm) | Concentration (ppm) |
| n-$C_{14}$ | 29126.09 | 1.14 | 29484.76 | 258.67 |
| Std | 25560.87 | 1.00 | 23215.87 | Nonpresent |
| n-$C_{15}$ | 27213.04 | 1.06 | 27691.21 | 478.17 |
| n-$C_{16}$ | 23010.87 | 0.90 | 23439.65 | 428.78 |
| n-$C_{17}$ | 18121.74 | 0.71 | 18505.57 | 383.83 |
| n-$C_{18}$ | 12404.35 | 0.49 | 12721.73 | 317.38 |
| n-$C_{19}$ | 7742.39 | 0.30 | 7987.07 | 244.68 |
| n-$C_{20}$ | 3985.87 | 0.16 | 4165.86 | 179.99 |
| n-$C_{21}$ | 1955.43 | 0.08 | 2077.77 | 122.34 |
| n-$C_{22}$ | 1020.65 | 0.04 | 1120.03 | 99.38 |
| n-$C_{23}$ | 494.57 | 0.02 | 570.21 | 75.64 |
| n-$C_{24}$ | 247.28 | 0.01 | 297.36 | 50.08 |
| n-$C_{25}$ | 104.35 | 0.00 | 145.03 | 40.68 |

* n-$C_{10\text{-}25}$ denote normal alkane hydrocarbons ranging in total carbon number from 10 to 25.
Std denotes 1-pentadecene internal standard which is added to the drilling fluids In the second stage, the detection of natural hydrocarbon in contaminated drilling cuttings is achieved as illustrated in the flowchart in FIG. 3. The drilling fluid used is already mixed with the synthetic chemical standard in the first stage, resulting in tagged oil-based drilling fluid. In a first step of the second stage (314), the tagged oil-based drilling fluid is circulated in the borehole while drilling via a mud pump. A mud pump, or mud dripping pump, is a reciprocating piston or plunger pump designed to circulate drilling fluid under high pressure down the drill string and back up and out the drilling bit. Referring back to FIG. 2, when the drilling bit (230) reaches the reservoir zone (232), the drilling cuttings from the reservoir layer (228) start to circulate to the surface and are retrieved from the shale shaker (202). This action corresponds to a second step of the second stage (316), which is recovery of rock cuttings mixed with tagged oil-based drilling fluid.

In one or more embodiments, samples are then transferred to the natural hydrocarbon detection unit (refer to (234) in FIG. 2), at which drilling cuttings are first subjected to intensive organic solvent extraction under preset pressure and temperature settings. Non-limiting examples of organic solvents which can be extracted include hexane, iso-octane, dichloromethane, carbon disulfide, and methanol. The organic solvent extraction, in a third step of the second stage (318), extracts all hydrocarbons present in the drilling cuttings sample in a fluid phase. The hydrocarbons removed include artificial hydrocarbons from the tagged oil-based drilling fluid and natural hydrocarbons from the oil-bearing reservoir rock, which together produce a fluid extract. In a fourth step of the second stage (320), the fluid extract is analyzed via gas chromatography-mass spectrometry (GC-MS) to measure the concentration of all hydrocarbons present in the drilling cuttings. The output of the instrument (i.e., a peak area of n-alkanes $C_{10+}$ (322) and a peak area of internal standard (324)) is then processed to calculate the concentration of all hydrocarbons (i.e., n-alkanes in ppm) in a fifth step of the second stage (326). Subsequently, the established calibration ratio factor from the fourth step (312) in the first stage is used to calculate the exact amount of hydrocarbons present in the drilling cuttings that result from drilling fluids (refer to Table 1 above for examples). The hydrocarbon signals from the tagged oil-based drilling fluid are then subtracted from the total hydrocarbon signal measured from the drilling cuttings fluid extracts in a hydrocarbon signal removal from oil-based drilling fluid step (328). Specifically, the subtraction process uses the known concentration of hydrocarbon in the drilling fluids prior to circulating them in the borehole and the hydrocarbon concentrations measured in the recovered drilling cuttings in order to derive the natural hydrocarbon signal. Therefore, the natural hydrocarbon signal is the initial drilling fluid hydrocarbon concentration subtracted from the hydrocarbon concentration of cuttings with drilling fluid. Non-limiting examples of these values are shown in Table 1 above. Finally, the method described herein results in a quantitative measurement of natural hydrocarbons (330).

Figure 4:
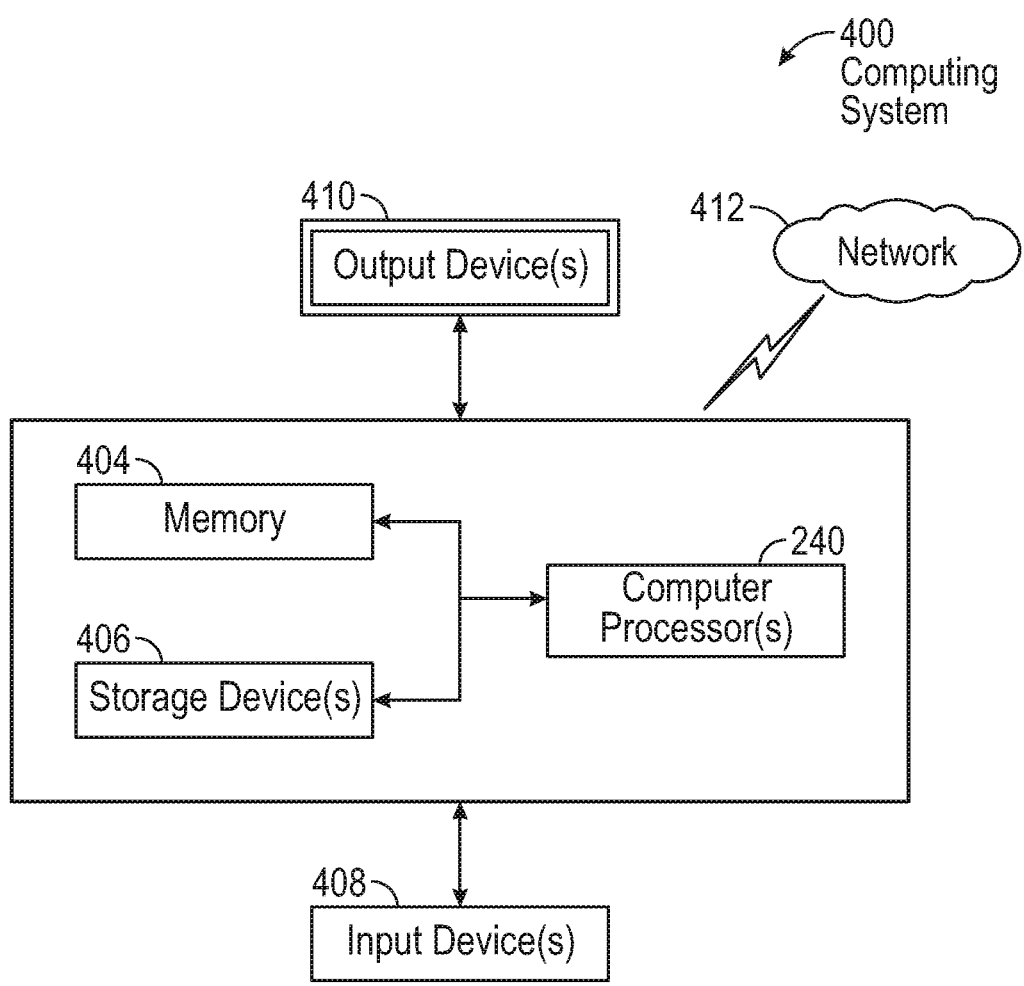
FIG. 4 is an illustration of a computing system according to embodiments of the present disclosure.

One or more embodiments may be implemented on a computing system. Any combination of mobile, desktop, server, router, switch, embedded device, or other types of hardware may be used. FIG. 4 illustrates an exemplary computing system (400). The computing system (400) may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments disclosed herein. For example, as shown in FIG. 4 the computing system (400) may include one or more computer processor(s), or a processing module (240), associated memory (404) (e.g., random access memory (RAM), cache memory, flash memory), one or more storage device(s) (406) (e.g., a hard disk, an optical drive such as a compact disk (CD) drive or digital versatile disk (DVD) drive, a flash memory stick), and numerous other elements and functionalities. The computer processor(s) (240) may be an integrated circuit for processing instructions. For example, the computer processor(s) may be one or more cores, or micro-cores of a processor.

The computing system (400) may also include one or more input device(s) (408), such as a camera, imager, touchscreen, keyboard, mouse, microphone, touchpad, electronic pen, or any other type of input device. Further, the computing system (400) may include one or more output device(s) (410), such as a screen (e.g., a liquid crystal display (LCD), a plasma display, touchscreen, cathode ray tube (CRT) monitor, or other display device), a printer, external storage, or any other output device. One or more of the output device(s) may be the same or different from the input device(s). The computing system (400) may be connected to a network (412) (e.g., a local area network (LAN), a wide area network (WAN) such as the Internet, mobile network, or any other type of network) via a network interface connection (not shown). The input and output device(s) may be locally or remotely (e.g., via the network (412)) connected to the computer processor(s) (240), memory (404), and storage device(s) (406). Many different types of computing systems exist, and the aforementioned input and output device(s) (408), (410) may take other forms.

Further, one or more elements of the computing system (400) may be located at a remote location and be connected to the other elements over a network (412). Further, one or more embodiments may be implemented on a distributed system having a plurality of nodes, where each portion of the embodiment may be located on a different node within the distributed system. In one embodiment, the node corresponds to a distinct computing device. In other embodiments, the node may correspond to a computer processor with associated physical memory. In yet other embodiments, the node may correspond to a computer processor or microcore of a computer processor with shared memory and/or resources.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

The invention described herein has multiple advantages over existing techniques. For instance, unlike prior techniques, the present invention is utilized to detect natural hydrocarbons in drilling cuttings, not crude oil samples. This aspect is significant because it enables flagging of potential oil and gas-bearing rock beds during drilling prior to any further testing. In addition, unique tagging compounds, that are similar in properties to natural hydrocarbons, are used in the present invention to tag oil-based drilling fluids. Unlike existing tracers, such as $C_{16}$ to $C_{20}$ alkenes, the invention described herein introduces 1-pentadecene of known concentration to the drilling fluids. This tagging will fixate the drilling fluid compounds concentration and can be used to measure the presence of natural hydrocarbons in drilling cuttings, prior to producing crude oil altogether. Furthermore, an ultra-sensitive analytical approach is utilized to detect hydrocarbons using GC-MS-QQQ technology, which is capable of detecting hydrocarbons at the femtogram level. GC-MS-QQQ analytical systems measure the mass of each hydrocarbon compound, thereby increasing the sensitivity and selectivity of the detected hydrocarbons compared to traditional GCxGC-FID analytical approaches.

In summary, the method according to embodiments of this disclosure adds a synthetic chemical standard to oil-based drilling fluid with known concentration to quantitatively remove the hydrocarbon overprint resulting from oil-based drilling fluid in order to reveal the natural hydrocarbon abundance in drilling cuttings. The method can also be applied for detection of hydrocarbon-bearing layers while drilling in real-time, reducing the need for costly downhole well-testing for hydrocarbons, and maximizing the extracted geological information from drill cuttings.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method for detecting the presence of natural hydrocarbon compounds in drilling cuttings, the method comprising:
   introducing a synthetic chemical standard having a known concentration to an oil-based drilling fluid;
   producing a tagged oil-based drilling fluid;
   using gas chromatography-mass spectroscopy, determining a concentration of hydrocarbon compounds present in the tagged oil-based drilling fluid, wherein the concentration corresponds to a first hydrocarbon signal;
   circulating the tagged oil-based drilling fluid in a borehole during drilling;
   recovering drilling cuttings mixed with the tagged oil-based drilling fluid from the borehole;
   extracting hydrocarbon compounds from the drilling cuttings;
   using gas chromatography-mass spectroscopy, determining a concentration of hydrocarbon compounds present in the drilling cuttings that were mixed with the tagged oil-based drilling fluid, wherein the concentration corresponds to a second hydrocarbon signal; and
   based on the difference between the first hydrocarbon signal and the second hydrocarbon signal, determining an initial concentration of natural hydrocarbons in the drilling cuttings prior to mixing with the tagged oil-based drilling fluid.

2. The method as set forth in claim 1, wherein the synthetic chemical standard is 1-pentadecene.

3. The method as set forth in claim 1, further comprising:
   analyzing the tagged oil-based drilling fluid using gas chromatography-mass spectroscopy, resulting in a peak area corresponding to hydrocarbon compounds and a peak area corresponding to the synthetic chemical standard; and
   determining a concentration of each individual hydrocarbon compound in parts per million according to the following:

$$\text{HC concentration} = \frac{HCa}{STa} \times STc \times F,$$

where HCa denotes the peak area corresponding to hydrocarbon compounds, STa denotes the peak area corresponding to the synthetic chemical standard, STc denotes the known concentration of the synthetic chemical standard, and F denotes an instrument response factor.

4. The method as set forth in claim 3, further comprising determining a calibration relationship for the hydrocarbon compounds, wherein the calibration relationship is a calibration ratio factor for the concentration of each individual hydrocarbon compound relative to the known concentration of the synthetic chemical standard.

5. The method as set forth in claim 4, further comprising using the calibration ratio factor to determine the concentration of hydrocarbon compounds present in the drilling cuttings that were mixed with the tagged oil-based drilling fluid.

6. A system for detecting the presence of natural hydrocarbon compounds in drilling cuttings, the system comprising:
   a drilling bit configured for cutting into rock in a borehole;
   a drilling cuttings collector configured for recovering drilling cuttings that were mixed with an oil-based drilling fluid tagged with a synthetic chemical standard having a known concentration during drilling;
   a hydrocarbon detection unit configured for extracting hydrocarbon compounds from the drilling cuttings;
   a gas-chromatograph equipped with a mass-spectrometer configured for:
      determining a concentration of hydrocarbon compounds present in the tagged oil-based drilling fluid, wherein the concentration corresponds to a first hydrocarbon signal;
      determining a concentration of hydrocarbon compounds present in the drilling cuttings that were mixed with the tagged oil-based drilling fluid, wherein the concentration corresponds to a second hydrocarbon signal; and
   a computing system configured for:
      determining, based on the difference between the first hydrocarbon signal from the second hydrocarbon signal, an initial concentration of natural hydrocarbons in the drilling cuttings prior to mixing with the tagged oil-based drilling fluid.

7. The system as set forth in claim 6, wherein the synthetic chemical standard is 1-pentadecene.

8. The system as set forth in claim 6, wherein the gas-chromatograph equipped with a mass-spectrometer is further configured for:
   analyzing the tagged oil-based drilling fluid using gas chromatography-mass spectroscopy, resulting in a peak area corresponding to hydrocarbon compounds and a peak area corresponding to the synthetic chemical standard, and
   wherein the computing system is further configured for:
      determining a concentration of each individual hydrocarbon compound in parts per million according to the following:

$$\text{HC concentration} = \frac{HCa}{STa} \times STc \times F,$$

where HCa denotes the peak area corresponding to hydrocarbon compounds, STa denotes the peak area corresponding to the synthetic chemical standard, STc denotes the known concentration of the synthetic chemical standard, and F denotes an instrument response factor.

9. The system as set forth in claim 8, wherein the computing system is further configured for determining a calibration relationship for the hydrocarbon compounds, wherein the calibration relationship is a calibration ratio factor for the concentration of each individual hydrocarbon compound relative to the known concentration of the synthetic chemical standard.

10. The system as set forth in claim 9, wherein the computing system is further configured for using the calibration ratio factor to determine the concentration of hydrocarbon compounds present in the drilling cuttings that were mixed with the tagged oil-based drilling fluid.

* * * * *